United States Patent [19]

Keith et al.

[11] 4,291,015

[45] Sep. 22, 1981

[54] POLYMERIC DIFFUSION MATRIX CONTAINING A VASODILATOR

[75] Inventors: Alec D. Keith, Miami, Fla.; Wallace Snipes, State College, Pa.

[73] Assignee: Key Pharmaceuticals, Inc., Miami, Fla.

[21] Appl. No.: 163,262

[22] Filed: Jun. 26, 1980

Related U.S. Application Data

[63] Continuation-in-part of Ser. No. 109,242, Jan. 3, 1980, which is a continuation-in-part of Ser. No. 2,565, Jan. 11, 1979, abandoned, and Ser. No. 47,084, Jun. 11, 1979, abandoned.

[30] Foreign Application Priority Data

Aug. 14, 1979 [JP]  Japan .................................. 54/103459

[51] Int. Cl.³ .................... A61L 15/03; A61K 31/21; A61K 31/79
[52] U.S. Cl. ..................................... 424/28; 128/268; 424/22; 424/80; 424/298
[58] Field of Search .................... 128/268; 424/22, 28, 424/80

[56] References Cited

U.S. PATENT DOCUMENTS

| | | | |
|---|---|---|---|
| 2,693,438 | 11/1954 | Ward | 424/28 |
| 2,776,924 | 1/1957 | Martin | 424/80 |
| 2,973,300 | 2/1961 | Farrar et al. | 424/80 |
| 3,073,742 | 1/1963 | Bolz et al. | 424/80 |
| 3,214,338 | 10/1965 | Ehrlich | 424/28 X |
| 3,287,222 | 11/1966 | Larde et al. | 424/28 |
| 3,598,123 | 10/1971 | Zaffaroni | 128/268 |
| 3,608,070 | 9/1971 | Nouvel | 424/80 |
| 3,731,683 | 5/1973 | Zaffaroni | 128/268 |
| 3,742,951 | 7/1973 | Zaffaroni | 128/268 |
| 3,972,995 | 8/1976 | Tsuk et al. | 424/28 |
| 4,076,798 | 2/1978 | Casey et al. | 424/22 |
| 4,210,633 | 7/1980 | Takruri et al. | 424/80 |

FOREIGN PATENT DOCUMENTS

| | | | |
|---|---|---|---|
| 764422 | 8/1971 | Belgium | 424/28 |
| 930668 | 7/1973 | Canada | 128/268 |
| 2224126 | 10/1974 | France | 424/80 |
| 2224140 | 10/1974 | France | 424/80 |
| 2437830 | 4/1980 | France . | |
| 53/7493 | 3/1978 | Japan | 424/28 |
| 54/15117 | 11/1979 | Japan | 424/28 |
| 1108837 | 4/1968 | United Kingdom . | |
| 2021950 | 12/1979 | United Kingdom . | |

*Primary Examiner*—Shep K. Rose
*Attorney, Agent, or Firm*—Wegner & Bretschneider

[57] ABSTRACT

A polymeric diffusion matrix containing a vasodilator is provided comprising from about 2 to about 60% of a polar plasticizer, e.g., glycerol, from about 2 to about 15% of a matrix component, e.g., polyvinylalcohol, from about 2 to about 10% of a water-soluble polymer with hydration sites, e.g., polyvinylpyrrolidone, which in combination with the remaining ingredients yields a matrix capable of sustained release of a vasodilator drug dispersed therein, and the balance water, the percentages being by weight.

25 Claims, No Drawings

POLYMERIC DIFFUSION MATRIX CONTAINING A VASODILATOR

CROSS-REFERENCE TO RELATED APPLICATIONS

This application is a continuation-in-part of U.S. Application Ser. No. 109,242, filed Jan. 3, 1980, which in turn is a continuation-in-part of U.S. Application Ser. No. 2,565, filed Jan. 11, 1979, now abandoned, and Ser. No. 47,084, filed June 11, 1979, now abandoned.

SUMMARY OF THE INVENTION

The present invention relates to a polymeric diffusion matrix containing a vasodilator. More particularly, the invention relates to a polymeric diffusion matrix containing a vasodilator characterized by a sustained release of the vasodilator. Furthermore, the polymeric diffusion matrix is self-supporting.

In one embodiment, a polymeric diffusion matrix is provided comprising from about 2 to about 60% glycerol, from about 2 to about 15% polyvinylalcohol, from about 2 to about 10% of a water-soluble polymer with hydration sites which in combination with the remaining ingredients (including a vasodilator) yields a matrix capable of sustained release of a vasodilator dispersed therein, and the balance water, the percentages being by weight. Preferably, the water-soluble polymer is polyvinylpyrrolidone. The polyvinylalcohol preferably has a molecular weight of from about 50,000 to about 150,000, particularly from about 100,000 to about 150,000 and the polyvinylpyrrolidone preferably has a molecular weight of from about 15,000 to about 80,000, particularly from about 20,000 to about 60,000. The glycerol is preferably present in an amount of about 35% to about 55%.

The glycerol (a polar plasticizer) in the diffusion matrix can be replaced in whole or in part with propylene glycol or polyalkylene glycols such as polyethylene glycol and polypropylene glycol. Polyethylene glycols particularly those having molecular weights ranging from about 200 to about 1,000 can be used as the polar plasticizer. If polyethylene glycol is used in admixture with glycerol, the glycol can have a molecular weight of up to about 4,000. It has been found that a polar plasticizer, e.g., glycerol is a necessary component in the matrix. A diffusion matrix formed with no polar plasticizer is not flexible and has poor diffusional contact with the skin causing unreliable diffusion release.

It is possible to replace the polyvinylalcohol matrix component with polymers of hydroxyethylacrylate, polymers of hydroxyethylmethacrylate, polymers of hydroxypropylacrylate, and polymers of hydroxypropylmethacrylate. It is possible to use homopolymers or copolymers of the hydroxyalkyl(meth)acrylates.

The water-soluble polymer can be (in addition to polyvinylpyrrolidone) any of agar, agarose, gum arabic, gum tragacanth, polyacrylic acid, polymethacrylic acid, polyvinyloxazolidone, polyvinylmorpholinone, and polyvinylpiperidone.

In a preferred embodiment, a polymeric diffusion matrix suitable for the transdermal delivery of a vasodilator is provided comprising from about 2 to about 60% glycerol, from about 2 to about 15% polyvinyl alcohol, from about 2 to about 10% of a water-soluble polymer with hydration sites which in combination with the remaining ingredients yields a matrix capable of sustained release of a vasodilator dispersed therein, and the balance water, the percentages being by weight. Preferably, the water-soluble polymer is polyvinylpyrrolidone. The polyvinylalcohol preferably has a molecular weight of from about 50,000 to about 150,000, particularly from about 100,000 to about 150,000 and the polyvinylpyrrolidone preferably has a molecular weight of from about 15,000 to about 80,000, particularly from about 20,000 to about 60,000.

DETAILED DESCRIPTION OF THE INVENTION

According to the present invention, a polymeric diffusion matrix is provided comprising, on a weight basis, from about 2 to about 60% glycerol, from about 2 to about 15% polyvinylalcohol, from about 2 to about 10% of a water-soluble polymer with hydration sites which is compatible with the remainder of the ingredients of the diffusion matrix to permit the sustained release of a vasodilator, the balance being water. This water-soluble polymer complements the polyvinylalcohol by providing retention of shape of the desired diffusion matrix. A representative example of a water-soluble polymer with hydration sites suitable for the present invention is polyvinylpyrrolidone. The matrix contains a therapeutically effective amount of a vasodilator for topical or transdermal application to a patient, thus forming a vasodilator drug delivery device.

In a first embodiment, the present invention provides a diffusion matrix for the application of a vasodilator to a patient (vasodilator drug delivery matrix). In another aspect of the present invention, the transdermal or topical application of vasodilator drugs is contemplated via the diffusion matrix. The diffusion matrix of the present invention provides a steady release of the drug to the patient over an extended period of time, typically 24 hours.

In the uncured matrix, the glycerol is present in an amount of from about 2 to 60%. When trinitroglycerol is the vasodilator to be applied, the amount of glycerol preferably should be within the range of from about 35 to 55%. Preferably, the glycerol has a minimum specific gravity of 1.23 g/ml.

The polyvinylalcohol is present in the uncured matrix in an amount of from about 2 to about 15%, preferably from about 4 to about 9% by weight. Preferably, the polyvinylalcohol has a molecular weight of at least about 70,000. Most preferably, the molecular weight is from about 100,000 to about 150,000.

The water-soluble polymer with hydration sites is present in the uncured matrix in an amount of from about 2 to about 10%, preferably from about 2 to about 5%, by weight. In a preferred embodiment, polyvinylpyrrolidone is used as the water soluble polymer. The molecular weight for the polyvinylpyrrolidone should be selected to maintain water solubility. In general, this molecular weight should be within the range of from about 15,000 to about 80,000, preferably from about 20,000 to about 60,000, and most preferably from about 35,000 to about 50,000. The polyvinylpyrrolidone may be replaced by other ingredients which permit sustained release. The balance of the matrix comprises essentially water.

In its cured state, the polymeric diffusion matrix comprises from about 2 to about 55%, preferably from about 4 to about 35% glycerol, from about 4 to about 30%, preferably from about 8 to about 20% polyvinylalcohol;

from about 2 to about 20%, preferably from about 4 to about 10%, of a water-soluble polymer having hydration sites, preferably polyvinylpyrrolidone, and the balance water, all percentages being by weight. The molecular weight ranges for the polyvinylalcohol and polyvinylpyrrolidone are the same for cured and uncured diffusion matrices. The cured matrix has a density of about 1.2 g/ml. It is noted that the weight ratio of glycerol to water in the cured matrix is about 0.6–1.8:1, preferably about 1:1. The cured matrix shows little swelling when immersed in water and will not dissolve in water at room temperature. However, if the water is heated to boiling, the diffusion matrix will dissolve.

At least one vasodilator is dispersed throughout the diffusion matrix when the diffusion matrix is used as a vasodilator drug delivery device. The type of vasodilator which may be dispersed in the diffusion matrix of the present invention includes any vasodilator which is capable of being transdermally or topically administered to a patient. When the sustained release of the drug at a relatively steady rate over a prolonged period, typically 24 hours, the patient is provided with the benefit of a steady application of the vasodilator over the prolonged period.

The vasodilators employed in the present invention generally include those agents suitable for systemic absorption through the external body skin in accordance with their known dosages and uses. Representative vasodilators are compounds having a nitrate ion. Representative vasodilators include amyl nitrate, nitroglycerin (trinitroglycerol), sodium nitrate, erythrityl tetranitrate, pentaerythritol tetranitrate, isosorbide dinitrate, mannitol hexanitrate, trolnitrate phosphate (triethanolamine biphosphate), and the like.

When trinitroglycerol is used, it is ordinarily present in the form of lactose triturate. It is necessary to have an active adsorbent surface for the trinitroglycerol. The active adsorbent surface can be supplied by lactose, insolubilized starch, micronized cellulose, silica gel, di- and oligosaccharides having a degree of solubility from lower than to up to twice that of lactose, and cyclitols.

When lactose is employed as the insoluble active adsorbent surface material, it is necessary to make certain there is enough polar plasticizer, e.g. glycerol and not too much water, as this would cause the lactose to become solubilized. Solubilization will prolong the setting time and may decrease adhesion to the backing.

The amount of the vasodilator dispersed in the diffusion matrix can be varied in accordance with the desired dosage and the length of time the matrix is to remain on the skin. However, the amount of the vasodilator included in the matrix should generally be in excess of the amount which is to be delivered to the patient. If the diffusion matrix is to be used for 24 hours, a suitable excess of the vasodilator should be included to assure appropriate release kinetics. For example, if it is desired to apply about 10 mg of trinitroglycerol to a patient over 24 hours, a roughly six-fold excess of the trinitroglycerol should be included in the diffusion matrix. Accordingly, from 50 to 70 mg is considered a preferred amount to provide a 10 mg release of trinitroglycerol over a 24-hour period. Quite obviously, the optimum amount that should be included in the diffusion matrix will vary according to factors such as the period of release of the drug.

In a preferred embodiment, there is used trinitroglycerol (also known as 1,2,3-propanetriol trinitrate or nitroglycerin), which is useful in coronary medicine as a vasodilator. It is preferred to add the trinitroglycerol in the form of lactose triturate, In addition, the ratio of lactose triturate to the water and glycerol should avoid proportions where the trinitroglycerol may separate and raise an explosion hazard. A preferred lactose triturate is a composition comprising 10% nitroglycerin and 90% beta-lactose.

In forming the trinitroglycerol-containing matrix, excess water is not required. Hence, this matrix comprises from about 35 to about 60%, preferably from about 45 to about 55% glycerol; from about 2 to about 15%, preferably from about 4 to about 9% polyvinylalcohol; from about 2 to about 10%, preferably from about 2 to about 5% polyvinylpyrrolidone, and the balance being essentially water, all percentages being by weight. The amount of water evaporated from the uncured matrix is negligible, hence, the higher percentage for the glycerol. For this matrix, the weight ratio of glycerol to total polymers is usually greater than 1, preferably from about 1.4 to 15:1.

The amount of trinitroglycerol which should be used is based upon a desired delivery of about 5 to 10 mg per patient over a 24-hour period. The diffusion matrix drug delivery system of the present invention to deliver the 5 or 10 mg in the 24-hour period should contain about 40 to 60 mg of the trinitroglycerol. To reach this objective, the concentration of the trinitroglycerol in the diffusion matrix and the area of the diffusion matrix are factors to consider. In accordance with a preferred aspect of the present invention, from about 0.1 to about 4.0% by weight trinitroglycerol is included in the diffusion matrix. In a preferred aspect of the present invention, 80 ml of the solution is mixed with 20 gm of lactose triurate; this mixture is mechanically stirred until it is homogenous. The resultant homogenous mixture is poured into forms preferably made of glass or stainless steel, these forms or templates producing a diffusion matrix having a thickness of about 3 to about 4 mm, in accordance with a preferred aspect of the present invention. This diffusion matrix is either cast or cut into pieces of the desired size. In a preferred aspect, squares of about one inch on each side, or about 6.5 cm$^2$, have been prepared for ease of application to the patient.

The following methods may be used for preparing the diffusion matrix of the present invention:

In a first method, the matrix is formed at atmospheric pressure. Water and glycerol are first mixed together. Since alkaline solutions of nitroglycerin or other organic nitrates have relatively poor stability, the pH of the glycerol/water mixture is adjusted so that it is either neutral or slightly acidic, i.e., the pH ranging from about 6.5 to about 7.0. In a preferred embodiment, the pH is adjusted to within the above-mentioned range by adding sodium citrate and citric acid to the mixture.

The polyvinylalcohol and polyvinylpyrrolidone are then added to the glycerol-water mixture at room temperature, with agitation. The mixture is heated to a temperature within the range of from about 90° to about 95° C. at atmospheric pressure to extend the polymers. The mixture is held at this temperature for about one hour. If desired, the mixture may be maintained at this temperature for a period of about 48 hours prior to the addition of the drug. Thus, the mixture is stable for a period of about 48 hours and may be kept for such a period before being mixed with the drug to be delivered to the patient. Thereafter, the mixture is cooled to 80° C. and stirred for an additional hour to remove bubbles from the mixture. The drug to be applied to the patient is then added to the mixture, with thorough agitation. Once a homogeneous mixture of the polymer solution and drug is obtained, the mixture is ready to be cast into sheets of the drug-containing diffusion matrix. In a preferred embodiment, the drug may be dissolved or dispersed by agitation in a suitable solvent such as glycerin and water. The thus-obtained solution can be maintained at room temperature for prolonged periods without deterioration.

In a second method, water and glycerol are mixed, with the pH of the mixture adjusted to a desired value by adding suitable amounts of sodium citrate and citric acid. Thereafter, the polyvinylalcohol and polyvinylpyrrolidone are added. The resulting mixture is then heated to a temperature of about 120° C. at a pressure of about 2 atmospheres absolute. The temperature is maintained for about 1 hour without any mechanical agitation. In a preferred embodiment, the heating may be performed in an autoclave. Since bubbles are not formed when the heating is conducted in an autoclave, such a procedure is preferred. Thereafter, the temperature is lowered to about 20 to about 80° C. whereupon the drug is to be applied to the patient is added. After the drug has been homogeneously dispersed in the fluid mixture, the mixture is poured into molds to form sheets of the drug-containing diffusion matrix.

In the above methods and for the case of trinitroglycerol and other drugs having similar limitations, the drug must be added and mixed thoroughly when the polymer mixture is in the liquid state. In the case of using lactose triturate the mixture should be cast within about 30 minutes after the drug has been introduced into the polymer solution. This is important in order to avoid the setting of the polymer solution prior to casting.

It has been found that curing is facilitated by subjecting the matrix to a temperature down to about $-20°$ C. immediately after casting. The setting period is quickened considerably.

The temperature at which the drug is to be added to the matrix solution depends on the stability and volatility of the drug. For example, trinitroglycerol begins to decompose at a temperature of above about 50° C. Accordingly, in preparing a trinitroglycerol-containing diffusion matrix, the matrix solution mixture is cooled to about 50° C., whereupon the trinitroglycerol is added. The drug-containing diffusion solution is then cast into molds to form sheets of the final product. In addition, for trinitroglycerol, the pH of the solution mixture should be kept slightly acidic, i.e., between 6.5 and 7.0 since trinitroglycerol is stablized within this pH range.

Sodium dodecyl sulfate or sorbitan (Tween-20) or other detergents may be added in an amount of 0.1 to 10% by weight, based on the matrix, as a dispersing agent, if desired.

For vasodilators that are alcohol-soluble, it may be desirable to add in the initial mixture of glycerol and water, ethanol or isopropanol in an amount of from 2 to 40% by weight, based on the matrix, to facilitate the preparation of a diffusion matrix for such alcohol-soluble drugs.

An absorption facilitator to insure skin penetration such as dimethylsulfoxide, decylmethylsulfoxide, or other penetration enhancers may be added.

If it is desired to increase the effective lifetime of the diffusion matrix, a drug reservoir may also be attached to the diffusion matrix. The diffusion matrix may also be used to help with local vasodilation to assist in the solution of physiological problems resulting from local circulatory deficiencies, for example, to promote circulation in the extremities of a patient.

The present drug delivery device comprises the drug-containing diffusion matrix and means for fastening the matrix to the skin of a patient. Such means can take various forms, such as an occlusive backing layer forming a kind of "bandage" with the diffusion matrix being held against the skin of a patient being treated. A polyethylene or Mylar tape is contemplated as one form of occlusive layer in accordance with the present invention. It can also take the form of an elastic band, such as a cloth band, a rubbery band or other material. Here, the diffusion matrix is placed directly on the skin and held in place by such elastic band which typically will be placed over the arm or wrist of the patient. An intermediate adhesive layer between the diffusion matrix and the skin capable of permitting the transdermal application of the drug can also be used.

As a preferred embodiment in the packaging of the present matrix, the drug-containing diffusion matrix is placed in a cavity provided in an inert backing material. Useful backing materials include metal foils such as aluminum foil, polyolefins such as polyethylene and polypropylene, polyesters such as Mylar (polyethylene terephthalate), polyamides such as nylon, and the like. The drug-containing diffusion matrix can be poured in its molten state into the cavity and permitted to cool. An adhesive layer is provided on the backing material surrounding the cavity. To prevent evaporative loss in the surface of the matrix, the adhesive layer and the matrix are sealed with a release layer. To use the device, the patient peels off the release layer and places the device in intimate contact with his skin. The exposed adhesive layer secures the device to the patient. A concentration gradient existing normal to the surface of the matrix and the patient's skin facilitates diffusion of the drug through the matrix into the patient's body. Thus, there is provided a device whereby a drug is delivered transdermally to a patient at a steady rate over a prolonged period of time. To apply the drug to the patient, the cover layer is peeled off. The exposed matrix is then taped onto a suitable portion of the patient's body, e.g. arm or wrist, to allow the drug to diffuse thereinto.

In the preferred embodiment wherein trinitroglycerol is dispersed in the polymeric diffusion matrix, the molten matrix is cast into cavities provided in the backing member. The matrix is permitted to cure for a short period (e.g. about 10 minutes to about one hour) and is sealed by placing the cover layer over the backing member.

The method of administration of this invention is suitable also for adaptation to buccal and especially to sublingual administration. Because of the much higher rate of absorption through the mucosa by that route, much shorter periods of administration are required.

The invention is illustrated by the following non-limiting Examples:

EXAMPLE I

Glycerol (45 ml), water (45 ml) and 1% by weight sodium citrate are mixed together and the pH adjusted to 7 through addition of sodium citrate and citric acid. This mixture is heated to 90° C.; after reaching at least 70° C. there are slowly added 7 gm polyvinyl alcohol (PVA 100% hydrolyzed, molecular weight 115,000) and 5 gm polyvinylpyrrolidone (mw 40,000). The mixture is stirred at 90° C. until solution is effected, which may take about 10 minutes, it being appreciated that with larger quantities, a considerably longer period of time may be needed. 80 ml of this solution are then mixed with 20 gm lactose triturate (10% nitroglycerin and 90% lactose), this mixture then being mechanically stirred until homogenous. The homogenous mixture is then poured into forms made of glass or stainless steel which serve as templates to produce a diffusion matrix having a thickness of about 3 to 4 mm. This diffusion matrix is then cut into square pieces of about 1 inch on each side, i.e., to provide a total surface area of about 6.5 cm$^2$.

To establish that a polar plasticizer such as glycerol is a necessary matrix component, a drug-free diffusion matrix of Example I and a drug-free matrix of Example I without a glycerol component were prepared. Both matrices were doped with crystal violet. When applied to human skin, the matrix containing glycerol displayed a uniform color transfer from the surface of the diffusion matrix to the surface of the skin. The glycerolfree matrix, when applied to human skin, gave a spotty diffusion pattern. This is believed to establish that a polar plasticizer is a necessary element of the diffusion matrix of the instant invention in order to achieve uniform diffusion characteristics.

Rather than pouring the homogeneous mixture in Example I into forms, injection molding can be used. In injection molding, the foil backing is placed in a series of molds and the polymeric mixture is injection molded therein to form the final product.

A preferred foil is a "polyfoil" having consecutive layers of polyethylene, aluminum, polyethylene, polyester (polyethylene terephthalate). The first polyethylene layer has the diffusion matrix adhered thereto and the polyester layer represents the backing layer. A particularly preferred "polyfoil" is Ludlow CX-220 available from the Ludlow, Co., Ludlow, Mass.

Although the polyvinylalcohol of Example I was 100% hydrolyzed, it is possible to use partially hydrolyzed polyvinylalcohols. Tests have been conducted using 75, 88, 96, 97, 98, and 99% hydrolyzed polyvinyl-alcohols. With hydrolysis levels below 90%, some structural weakness, shrinkage, and even some phase separation are observed. It is preferred to use polyvinyl-alcohols that are at least 90%, preferably 95%, hydrolyzed.

EXAMPLE II

Example I is repeated with the exception that 3 gm of agar is used instead of polyvinylpyrrolidone. Calcium chloride is included in the mixture also and is present in an amount of 1% by weight.

EXAMPLE III

The diffusion matrix of Example I is applied to a patient by placing it against the wrist, shoulder or other sites of the patient.

EXAMPLE IV

The diffusion matrix of Example I is applied to a patient by first attaching the diffusion matrix to a Mylar or polyethylene backing layer. This occlusive backing layer is provided with an adhesive whereby the diffusion matrix is held in contact with the skin as part of this "bandage".

EXAMPLE V 948 g of 96% glycerol and 644 g of water are mixed together. 27 g of sodium citrate, 159 g of polyvinyl alcohol (molecular weight 115,000), 93 g of polyvinylpyrrolidone (molecular weight 40,000) are dissolved in the glycerol/water mixture by continuous stirring and maintaining at a temperature of about 90° C.

In a separate container, 600 g of lactose triturate (10% nitroglycerin and 90% lactose) is dispersed in 315 g glycerol and 214 g water with agitation at room temperature.

When the polymers have gone into solution, the lactose triturate dispersion is poured therein. The mixture is mixed thoroughly at a temperature range of between 50° and 55° C. to form a homogeneous mixture. The container is kept covered.

The homogeneous mixture is poured into forms made of glass or stainless steel which serve as templates to produce a drug-containing diffusion matrix having a thickness of about 3 to 4 mm. This diffusion matrix is then cut into square pieces of about 1 inch on each side, i.e. to provide a total surface area of about 6.5 cm$^2$.

EXAMPLE VI

Example V is repeated except that sodium polyacrylate having a molecular weight of 100,000 (a preferred molecular weight range of the polyacrylic acid or salt polymer) is used instead of polyvinylpyrrolidone.

EXAMPLE VII

Male dogs are anesthetized with sodium pentothal. Through surgical incisions, catheters are positioned in the femoral veins of each hind leg and in the abdominal aorta. Flow gauges are placed on the internal iliacs of both hind limbs. On a well-shaved area of the medial surface of the left thigh, a nitroglycerin-containing polymer matrix obtained in Example I is taped in place and remains undisturbed for 4 hours. The right hind limb receives no matrix or treatment of any kind. After application of the matrix, blood samples (5 ml) are taken from the catheters in each of the femoral veins and from that in the abdominal aorta at 15, 30, 60, 120, 180, and 240 minutes. Once drawn, the blood samples are put in ice, centrifuged (for 10 minutes) at 0° C., and 2 ml plasma is transferred to a silanized (with an alkylated silicone oil) glass tube. To each tube, 5 ml n-pentane is also added and the nitroglycerin is extracted for 1 hour with gentle shaking at 0° C. The pentane phase is then transferred to a 5 ml capacity Reacti-Vial$^{TM}$ and evaporated to near dryness. The residue is then dissolved in 30 microliters benzene containing 2 nanograms para-nitroanisole used as the external standard. 1.0 to 50.0 microliters of this solution is then injected for nitroglycerin quantitation using GLC-Electron Capture Detection. (A Hewlett-Packard 4610A Gas chromatograph equipped with a $^{63}$Ni-electron capture detector.) Separation is achieved on a 4 foot × 3 mm I.D. glass column packed with 10% SE-30 on 100/120 mesh GASCHROM QTM. The column is maintained at 140° C. while the injection-port temperature is 170° C. and the detector temperature is 220° C. A nitroglycerin calibration curve is constructed from the analyses of nitroglycerin-spiked blank plasma.

The results from the above test runs, summarized in Table 1, show dramatically that nitroglycerin is absorbed transepidermally from the matrix over the entire 4 hour period. Also, the levels attained in the venous blood draining the limb containing the matrix are approximately proportional to the matrix surface area in contact with the skin.

From the results of the studies here discussed, it is evident that transepidermal nitroglycerin absorption has occurred from the matrix to blood.

The nitroglycerin absorption rate appears to be fairly constant from 30-240 minutes are depicted by the essentially non-varying arterial nitroglycerin plasma levels.

TABLE I

| MATRIX SIZE-<br>STUDY No.<br>SAMPLE | 2" × 3"<br>1 | 2" × 1"<br>2 | 1" × 1"<br>3 |
|---|---|---|---|
| | nanograms nitroglycerin per ml. plasma | | |
| ARTERIAL-15 min. | 0.7 | 0.1 | 0.3 |
| ARTERIAL-30 min. | 0.6 | 0.2 | 0.5 |
| ARTERIAL-60 min. | 0.7 | 0.2 | — |
| ARTERIAL-120 min. | 0.9 | 0.5 | 0.4 |
| ARTERIAL-180 min. | 1.3 | 0.7 | 0.5 |
| ARTERIAL-240 min. | 1.3 | 0.2 | 0.3 |
| EXPERIMENTAL | | | |
| VENOUS-15 min. | 1.0 | 5.7 | 0.4 |
| VENOUS-30 min. | 0.5 | 8.3 | 0.3 |
| VENOUS-60 min. | 15.3 | 11.4 | 0.5 |
| VENOUS-120 min. | 26.9 | 7.6 | 0.8 |
| VENOUS-180 min. | 32.9 | 13.7 | 0.6 |
| VENOUS-240 min. | 32.0 | 5.6 | 0.2 |
| CONTROL | | | |
| VENOUS-15 min. | 0.4 | 9.2 | 0.1 |
| VENOUS-30 min. | 0.6 | 21.6 | 0.2 |
| VENOUS-60 min. | 7.4 | 4.5 | 0.3 |
| VENOUS-120 min. | 2.3 | 13.0 | 0.4 |
| VENOUS-180 min. | 9.9 | 14.5 | 0.4 |
| VENOUS-240 min. | 13.9 | 4.1 | 0.2 |

EXAMPLE VIII

Five male mongrel dogs, free of disease, are anesthetized with sodium pentobarbital. Under a septic surgical procedure, a catheter is inserted into the right atrium via the jugular vein for the removal of blood samples from the right heart. An arterial catheter is placed in the right carotid artery for the continuous recording of arterial blood pressure. Both catheters are exteriorized at the back of the neck.

The animals are allowed to recover from the anesthetic and are studied 24 hours later in the fasted, conscious state while resting comfortably in a supporting harness.

Each animal is allowed to become familiar with the laboratory surroundings and when completely acclimated, a 20 ml reference blood sample is obtained from the right heart catheter. A 1.0"×1.0" square of the nitroglycerin-containing polymer matrix obtained in Example I is then applied to a wellshaved area of the right lateral chest wall. The matrix is held securely in place with surgical tape. After application of the polymer matrix, 5.0 ml blood samples are obtained at: 15 min, 30 min, 45 min, 1 hr, 2 hr, 3 hr, 4 hr, 5 hr, 6 hr, 7 hr, 8 hr, 9 hr, 10 hr, 11 hr, 12 hr, 14 hr, 16 hr, 18 hr, 20 hr, 22 hr, and 24 hr. The animals are conscious and unrestrained during the entire 24 hour period of sampling. At no time do the animals display any unfavorable effects due to the transcutaneous administration of nitroglycerin.

Immediately after drawing, blood samples are put in ice and transferred to a walk-in refrigerator and centrifuged for 10 minutes at 0° C. A 2 ml aliquot of plasma is taken from each specimen and transferred to individual silanized (with an alkylated silicone oil) glass tubes. A 5 ml volume of n-pentane is added to each tube and the nitroglycerin is extracted for 60 minutes with gentle shaking at 0° C. The pentane phase is transferred to a 5 ml capacity Reacti-Vial and evaporated to near dryness. The residue is dissolved in 30 microliters of benzene containing 2 nanograms of para-nitro-anisole used as the external standard. A 1.0 to 5.0 microliter aliquot of this solution is injected for nitroglycerin quantitation using GLC-Electron Capture Detection (Hewlett-Packard 4610A Gas Chromatograph equiped with a 63Ni-electron capture detector.) Separation is achieved on a 4 foot×3 mm I.D. glass column packed with 10% SE-30 on 100/120 mesh GAS-Chrom QTM. The column is maintained at 140° C. while the injection-port temperature is 170° C. and detector temperature: 220° C. A nitroglycerin calibration curve is constructed from the analyses of nitroglycerin-spiked blank plasma.

Table 2 summarizes the plasma nitroglycerin data from the dogs. At each time point the mean ± the standard deviation is listed in the Table.

TABLE 2

| HOURS POST APPLICATION | ng nitroglycerin/ml. plasma | | | | | | |
|---|---|---|---|---|---|---|---|
| | DOG #1 | DOG #2 | DOG #3 | DOG #4 | DOG #5 | 5 DOGS | +/−S.D. |
| 0.25 | 0.1 | 0.4 | — | 0.4 | — | 0.3 | 0.1 |
| 0.50 | 0.1 | 0.3 | 0.0 | 0.2 | 0.2 | 0.1 | 0.1 |
| 0.75 | 0.1 | 0.3 | 0.0 | 0.1 | 0.2 | 0.1 | 0.1 |
| 1.00 | 0.2 | 0.2 | 0.2 | 0.1 | 0.4 | 0.2 | 0.1 |
| 2.00 | 0.2 | 0.6 | 0.0 | 0.2 | 0.3 | 0.3 | 0.2 |
| 3.00 | 2.1 | 0.4 | 0.0 | 0.9 | 0.2 | 0.7 | 0.8 |
| 4.00 | 0.5 | 0.8 | 0.1 | 0.3 | 0.3 | 0.4 | 0.3 |
| 5.00 | 0.2 | 1.0 | 0.3 | 0.2 | 0.1 | 0.4 | 0.4 |
| 6.00 | 0.2 | 0.6 | 0.2 | 0.6 | 0.9 | 0.5 | 0.3 |
| 7.00 | 0.9 | 0.7 | 0.5 | 0.3 | 1.2 | 0.7 | 0.4 |
| 8.00 | 0.2 | 2.4 | 0.7 | 0.4 | 0.5 | 0.8 | 0.9 |
| 9.00 | 0.2 | 0.6 | 0.3 | 0.3 | 0.1 | 0.3 | 0.2 |
| 10.00 | 0.1 | 0.8 | 0.6 | 0.3 | 0.7 | 0.5 | 0.3 |
| 11.00 | 0.1 | 0.8 | 0.1 | 0.4 | 0.5 | 0.4 | 0.3 |
| 12.00 | 0.4 | 0.6 | 0.4 | 0.3 | 0.1 | 0.3 | 0.2 |
| 14.00 | 0.0 | 0.4 | 0.2 | 0.2 | 0.2 | 0.2 | 0.1 |
| 16.00 | 0.1 | 0.4 | 0.3 | 0.6 | 0.3 | 0.4 | 0.2 |
| 18.00 | 0.3 | 1.2 | 0.3 | 0.3 | 0.4 | 0.5 | 0.4 |
| 20.00 | 0.3 | 0.4 | 0.5 | 0.3 | 0.2 | 0.3 | 0.1 |
| 22.00 | 0.2 | 1.1 | 0.7 | — | — | 0.7 | 0.5 |
| 24.00 | 0.3 | 0.4 | — | — | — | 0.4 | 0.1 |

It should be noted that if the data of the animal tests reported supra are plotted graphically, the data show that there is still a substantial release of the drug to the subject even after 24 hours. It is believed that the fluctuations in the individual readings with the five dogs tested is at least in part due to deficiencies in testing procedures and measurement techniques. Subsequent to the animal testing referred to above, there have been clinical trials using the polymeric diffusion matrix of Example V on several patients and these clinical trials also establish that the drug is released over a 24-hour period via the transdermal route.

What is claimed is:

1. A self-supporting polymeric diffusion matrix suitable for the transdermal delivery of a vasodilator comprising from about 2 to about 60% of the polar plasticizer selected from the group consisting of glycerol, propylene glycol, and a polyalkylene glycol, from about 2 to about 15% of a matrix component selected from the group consisting of polyvinylalcohol, a polymer of hydroxyethylacrylate, a polymer of hydroxyethylmethacrylate, a polymer of hydroxypropylacrylate, and a polymer of hydroxypropylmethacrylate, from about 2 to about 10% of a water-soluble polymer with hydration sites which in combination with the remaining ingredients yields a matrix capable of sustained release of a vasodilator dispersed therein, at least one vasodilator suitable for transdermal delivery to a patient, and the balance water, the percentages being by weight.

2. The polymeric diffusion matrix of claim 1 wherein said water-soluble polymer is selected from the group consisting of polyvinylpyrrolidone, agar, agarose, gum arabic, gum tragacanth, polyacrylic acid, polymethacrylic acid, polyvinyloxazolidone, polyvinylmorpholinone, and polyvinylpiperidone.

3. The polymeric diffusion matrix of claim 2 wherein said water-soluble polymer is polyvinylpyrrolidone.

4. The polymeric diffusion matrix of claim 3 wherein said matrix component is polyvinylalcohol having a molecular weight of from about 50,000 to about 150,000.

5. The polymeric diffusion matrix of claim 4 wherein said polyvinylalcohol has a molecular weight of from about 100,000 to about 150,000.

6. The polymeric diffusion matrix of claim 3 wherein said polyvinylpyrrolidone has a molecular weight of from about 20,000 to about 60,000.

7. The polymeric diffusion matrix of claim 3 wherein said matrix component is polyvinylalcohol having a molecular weight of from about 100,000 to about 150,000 and said polyvinylpyrrolidone has a molecular weight of from about 20,000 to about 60,000.

8. The polymeric diffusion matrix of claim 1 wherein said vasodilator is trinitroglycerol.

9. The polymeric diffusion matrix of claim 1 wherein said vasodilator is lactose triturate.

10. The polymeric diffusion matrix of claim 1 wherein said vasodilator is nitroglycerin and said nitroglycerin is attached to an active absorbent surface.

11. The polymeric diffusion matrix of claim 10 wherein said absorbent surface is provided by a member selected from the group consisting of lactose, insolubilized starch, micronized cellulose, silica gel, di- and oligosaccharides having a degree of solubility from lower than up to twice that of lactose, and cyclitols.

12. A self-supporting polymeric diffusion matrix suitable for the delivery of a drug having a vasodilator effect comprising from about 35 to about 60% glycerol, from about 4 to about 9% polyvinylalcohol, from about 2 to about 5% of a water-soluble polymer with hydration sites which in combination with the remaining ingredients yields a matrix capable of sustained release of a vasodilator drug dispersed therein, a therapeutically effective amount of trinitroglycerol and the balance water, the percentages being by weight.

13. The polymeric diffusion matrix of claim 12 wherein said water-soluble polymer is polyvinylpyrrolidone having a moleculr weight of from about 20,000 to about 60,000.

14. The polymeric diffusion matrix of claim 12 wherein said glycerol is present in an amount of from about 45 to about 55%.

15. The polymeric diffusion matrix of claim 8 wherein said polyvinylalcohol has a molecular weight of from about 100,000 to about 150,000.

16. A method of delivering a vasodilator drug to a patient over a prolonged period at a steady rate which comprises applying to said patient a self-supporting polymeric diffusion matrix suitable for the transdermal delivery of a vasodilator drug, said mixture comprising from about 2 to about 60% of a polar plasticizer compound selected from the group consisting of glycerol, propylene glycol, and a polyalkylene glycol, from about 2 to about 15% of a matrix component selected from the group consisting of polyvinyl alcohol, a polymer of hydroxyethylacrylate, a polymer of hydroxyethylmethacrylate, a polymer of hydroxypropylacrylate, and a polymer of hydroxypropylmethacrylate, from about 2 to about 10% of a water-soluble polymer with hydration sites which in combination with the remaining ingredients yields a matrix capable of sustained release of a vasodilator drug dispersed therein, at least one vasodilator drug suitable for transdermal delivery to said patient, and the balance water, the percentages being by weight.

17. The method of claim 16 wherein said vasodilator drug is trinitroglycerol.

18. The method of claim 17 wherein said water soluble polymer in said matrix is polyvinylpyrrolidone, said polyvinylpyrrolidone having a molecular weight of from about 20,000 to about 60,000.

19. The method of claim 17 wherein said matrix component is polyvinylalcohol having a molecular weight of from about 100,000 to 150,000.

20. A self-supporting polymeric diffusion matrix for the sustained release of trinitroglycerol to a patient by transdermal application, said matrix comprising
  (a) from about 2 to about 60% by weight glycerol;
  (b) from about 2 to about 15% by weight polyvinylalcohol;
  (c) from about 2 to about 10% by weight polyvinylpyrrolidone; and
  (d) a pharmaceutically effective amount of trinitroglycerol.

21. A self-supporting polymeric diffusion matrix for the sustained release of trinitroglycerol to a patient for transdermal application, said matrix comprising
  (a) from about 35 to about 55% by weight glycerol;
  (b) from about 4 to about 15% by weight polyvinylalcohol having a molecular weight of from about 100,000 to about 150,000;
  (c) from about 2 to about 10% by weight polyvinylpyrrolidone having a molecular weight of from about 20,000 to about 60,000; and
  (d) a pharmaceutically effective amount of trinitroglycerol.

22. The polymeric diffusion matrix of claim 21 formed from an aqueous mixture.

23. A self-supporting polymeric diffusion matrix for the sustained release of trinitroglycerol to a patient by transdermal application, said matrix containing about equal parts water and glycerol, about 7% by weight polyvinylalcohol having a molecular weight of abiout 115,000, about 5% by weight polyvinylpyrrolidone having a molecular weight of about 40,000, and a pharmaceutically effective amount of trinitroglycerol.

24. The polymeric diffusion matrix of claim 23 wherein said trinitroglycerol is present in the form of lactose triturate.

25. A self-supporting polymeric diffusion matrix suitable for the transdermal delivery of a drug, said matrix comprising
(a) from about 2 to about 60% of a polar plasticizer selected from the group consisting of glycerol, propylene glycol, and a polyalkylene glycol;
(b) from about 2 to 15% of a matrix component selected from the group consisting of polyvinylalcohol, a polymer of hydroxyethyacrylate, a polymer of hydroxyethylmethacrylate, a polymer of hydroxypropylacrylate, and a polymer of hydroxypropylmethacrylate;
(c) from about 2 to about 10% of a water-soluble polymer with hydration sites, which in combination with the remaining ingredients yields a matrix capable of sustained release of a drug dispersed therein; and
(d) the balance water, the percentages being by weight.

* * * * *